US 11,166,851 B2

(12) United States Patent
Foesel

(10) Patent No.: US 11,166,851 B2
(45) Date of Patent: Nov. 9, 2021

(54) CONTROLLING THE POSITION OF THE FOCAL POINT OF A LASER BEAM

(71) Applicant: Alcon Inc., Fribourg (CH)

(72) Inventor: Matthias Foesel, Memmelsdorf (DE)

(73) Assignee: Alcon Inc., Fribourg (CH)

( * ) Notice: Subject to any disclaimer, the term of this patent is extended or adjusted under 35 U.S.C. 154(b) by 46 days.

(21) Appl. No.: 16/683,680

(22) Filed: Nov. 14, 2019

(65) Prior Publication Data

US 2020/0229976 A1 Jul. 23, 2020

Related U.S. Application Data

(60) Provisional application No. 62/794,005, filed on Jan. 18, 2019.

(51) Int. Cl.
*G02B 27/28* (2006.01)
*A61F 9/008* (2006.01)
*G02B 5/30* (2006.01)
*G02B 27/09* (2006.01)
(Continued)

(52) U.S. Cl.
CPC ........ *A61F 9/0084* (2013.01); *A61F 9/00836* (2013.01); *G02B 5/3083* (2013.01); *G02B 27/0983* (2013.01); *G02B 27/286* (2013.01); *G02B 27/30* (2013.01); *A61B 2018/20359* (2017.05); *A61B 2018/20553* (2017.05); *A61B 2018/205547* (2017.05); *A61F 2009/00878* (2013.01); *A61F 2009/00897* (2013.01)

(58) Field of Classification Search
CPC .................... G02B 5/3083; G02B 27/0983
See application file for complete search history.

(56) References Cited

U.S. PATENT DOCUMENTS 7,982,169 B2  7/2011  Kittelmann
8,425,496 B2  4/2013  Vogler
8,439,902 B2  5/2013  Warm
(Continued)

FOREIGN PATENT DOCUMENTS

CN   106994557 B   10/2018
WO   2014/207751 A2  12/2014

OTHER PUBLICATIONS

MFC Series High-Speed Adjustable Focus Mirrors, 2017, 2 pages., Revibro Optics, LLC (www.revibrooptics.com).

*Primary Examiner* — Allen Porter
*Assistant Examiner* — Skylar Lindsey Christianson

(57) ABSTRACT

In certain embodiments, a system for controlling a position of a focal point of a laser beam comprises a beam expander, a scanner, an objective lens, and a computer. The beam expander controls the focal point of the laser beam and includes a mirror and expander optical devices. The mirror has a surface curvature that can be adjusted to control a z-position of the focal point. The expander optical devices direct the laser beam towards the mirror and receive the laser beam reflected from the mirror. The scanner receives the laser beam from the beam expander and manipulates the laser beam to control an xy-position of the focal point. The objective lens receives the laser beam from the scanner and directs the beam towards the target. The computer receives a depth instruction, and sets actuation parameters to control the surface curvature of the mirror according to the depth instruction.

12 Claims, 4 Drawing Sheets

(51) Int. Cl.
*G02B 27/30* (2006.01)
*A61B 18/20* (2006.01)

(56) References Cited

U.S. PATENT DOCUMENTS

| | | |
|---|---|---|
| 9,393,157 B2 | 7/2016 | Warm |
| 2007/0165312 A1 | 7/2007 | Aoki |
| 2008/0186551 A1 | 8/2008 | Hanft et al. |
| 2009/0127429 A1 | 5/2009 | Kittelmann |
| 2010/0004641 A1 | 1/2010 | Frey |
| 2010/0262128 A1 | 10/2010 | Vogler |
| 2010/0315605 A1 | 12/2010 | Arita |
| 2010/0318073 A1 | 12/2010 | Vogler |
| 2011/0028948 A1 | 2/2011 | Raksi |
| 2011/0110204 A1 | 5/2011 | Hashizume |
| 2012/0083771 A1 | 4/2012 | Warm |
| 2013/0169971 A1* | 7/2013 | Brown ............... G01B 9/02063 356/479 |
| 2015/0036899 A1 | 2/2015 | Warm |
| 2018/0360657 A1* | 12/2018 | Bor ................... B23K 26/0648 |

* cited by examiner

CONTROLLING THE POSITION OF THE FOCAL POINT OF A LASER BEAM

TECHNICAL FIELD

The present disclosure relates generally to laser systems, and more specifically to systems and methods for controlling the position of the focal point of a laser beam.

BACKGROUND

In ophthalmological laser surgery, making precise cuts is important. For example, a laser assisted in-situ keratomileusis (LASIK) flap is typically created sufficiently near the Bowman's layer to avoid trauma caused by pulling back the flap, but sufficiently far from the Bowman's layer to avoid breaching the layer, so the flap is cut to a depth of approximately 80 micrometers ($\mu$m) to 500 $\mu$m, such as approximately 120 $\mu$m. As another example, the lenticule removed in a SMall Incision Lenticule Extraction (SMILE) procedure leaves the cornea with a curvature that is intended to provide refractive correction, so the lenticule must be precisely cut. Accordingly, to enable consistent, high-quality results, the focus point of the laser beam must be controllable within a precision of a few micrometers.

BRIEF SUMMARY

In certain embodiments, a system for controlling a position of a focal point of a laser beam comprises a beam expander, a scanner, an objective lens, and a computer. The beam expander controls the focal point of the laser beam and includes a mirror and expander optical devices. The mirror has a surface curvature that can be adjusted to control a z-position of the focal point. The expander optical devices direct the laser beam towards the mirror and receive the laser beam reflected from the mirror. The scanner receives the laser beam from the beam expander and manipulates the laser beam to control an xy-position of the focal point. The objective lens receives the laser beam from the scanner and directs the beam towards the target. The computer receives a depth instruction, and sets actuation parameters to control the surface curvature of the mirror according to the depth instruction.

In certain embodiments, a method for controlling a position of a focal point of a laser beam directed to a target comprises receiving a depth instruction at a computer, which sets actuation parameters to control the surface curvature of the mirror according to the depth instruction. A beam expander, which comprises a mirror and expander optical devices, receives the laser beam. The mirror has a surface curvature that can be adjusted to control a z-position of the focal point. The expander optical devices direct the laser beam towards the mirror, which reflects the laser beam with the surface curvature to control the z-position of the focal point. The expander optical devices receive the laser beam reflected from the mirror. A scanner receives the laser beam from the beam expander and manipulates the laser beam to control an xy-position of the focal point. An objective lens receives the laser beam from the scanner and directs the beam towards the target.

Embodiments of the systems and methods may include one, two, or more of any of the following features in any suitable combination:

A polarizer is configured to: receive the laser beam with a first linear polarization; direct the laser beam with the first linear polarization towards a waveplate; receive the laser beam with a second linear polarization; and pass through the laser beam with the second linear polarization.

A waveplate is configured to: receive the laser beam from a polarizer with the first linear polarization; direct the laser beam towards the mirror; receive the laser beam reflected from the mirror; and convert the laser beam reflected from the mirror to the second linear polarization rotated relative to the first linear polarization.

A difference between the first and second polarizations is 90 degrees.

A waveplate comprises a quarter-wave plate configured to: receive the laser beam from the polarizer with the first linear polarization; convert the laser beam from the first linear polarization to a circular polarization; direct the laser beam towards the mirror; receive the laser beam reflected from the mirror; and convert the laser beam reflected from the mirror from the circular polarization to the second linear polarization.

A waveplate comprises a half-wave plate configured to: receive the laser beam from the polarizer with the first linear polarization; rotate the first linear polarization by 45 degrees; direct the laser beam towards the mirror; receive the laser beam reflected from the mirror; and rotate the polarization of the laser beam reflected from the mirror by 45 degrees to the second linear polarization.

A collimator is configured to: collimate the laser beam; and direct the laser beam towards the scanner.

A depth instruction specifies the z-position for the focal point.

A depth instruction is an instruction to increase or decrease from the current z-position of the focal point.

BRIEF DESCRIPTION OF THE DRAWINGS

Embodiments of the present disclosure are described by way of example in greater detail with reference to the attached figures, in which:

FIGS. 2A and 2B illustrate a cross-sectional view of a mirror, and FIG. 2C illustrates an example of an electrode plate of a mirror.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
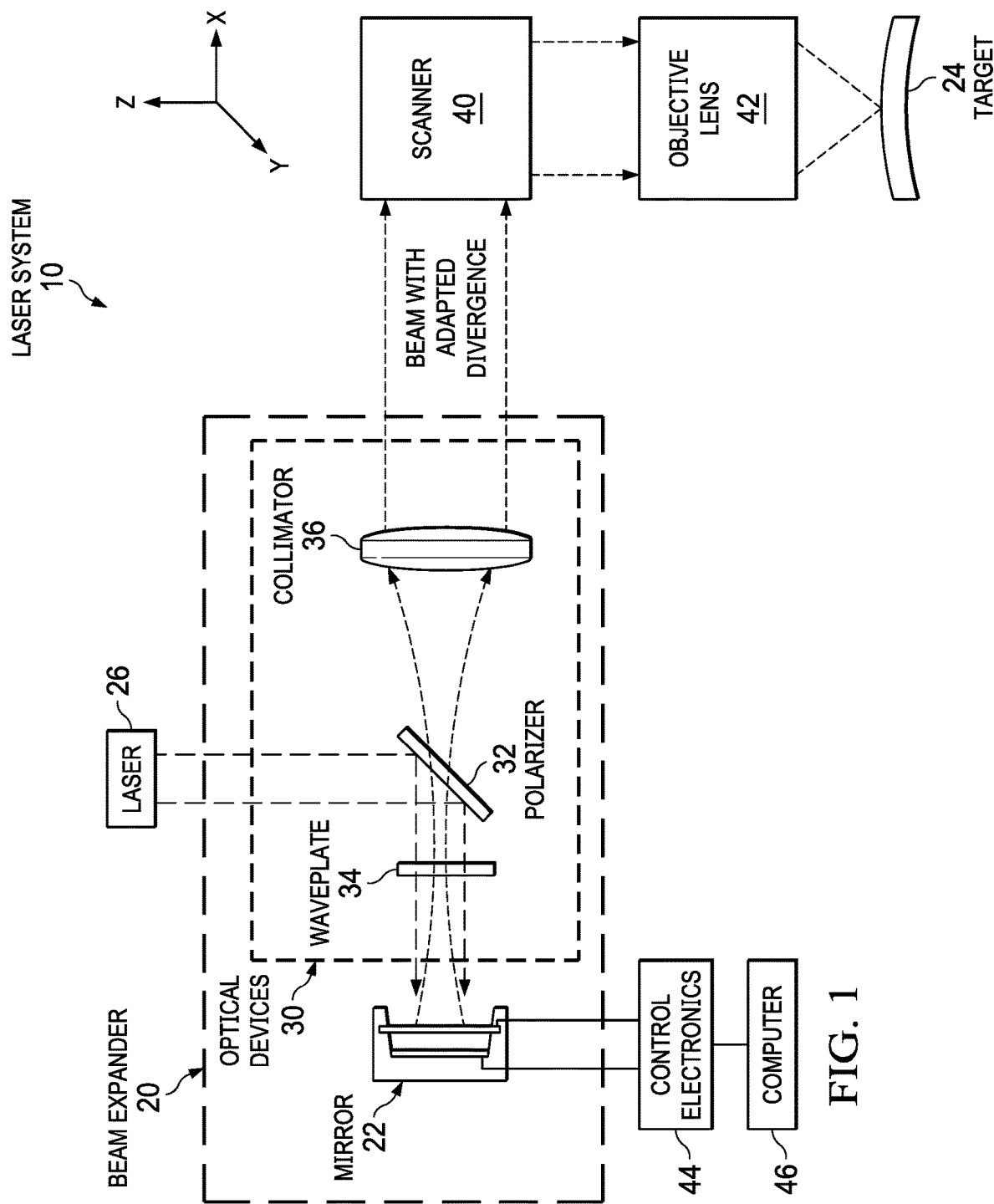
FIG. 1 illustrates an embodiment of a laser system that can control the position of the focal point of a laser beam directed to a target.

FIG. 1 illustrates an embodiment of a laser system 10 that can control the position of the focal point of a laser beam directed to a target 24. Laser system 10 includes a beam expander 20 that expands the laser beam. Beam expander 20 has a mirror 22 with a surface curvature that can be changed by applying voltage to electrodes of mirror 22. Changing the curvature changes the z-position of the focal point of the laser beam, which changes the depth of the laser beam within target 24.

In the illustrated embodiment, laser system 10 includes a laser 26 and beam expander 20, coupled as shown. Beam expander 20 comprises mirror 22 and optical devices 30, which include a polarizer 32, a waveplate 34, and a collimator 36, coupled as shown. Laser system 10 also includes a scanner 40, objective lens 42, control electronics 44, and a computer 46, coupled as shown. Laser system 10 may be used to perform an ophthalmic procedure on a part of an eye (e.g., the cornea of a human or animal eye) or a test material that mimics that part (e.g., poly(methyl methacrylate) (PMMA)).

According to an example of a method of that can be used with laser system 10, computer 46 receives a depth instruction and sets one or more actuation parameters for control electronics 44 to control the surface curvature of the mirror according to the depth instruction. Laser 26 generates a laser beam, which may be linearly polarized. Polarizer 32 of beam expander 20 receives and reflects the linearly polarized laser beam. Waveplate 34 receives the laser beam, converts the laser beam from linear polarization to circular polarization. Mirror 22 receives and reflects the laser beam with the surface curvature controlled according to the depth instruction. Waveplate 34 receives the reflected laser beam and converts the laser beam reflected from the mirror from the circular polarization to linear polarization, where this linear polarization is rotated relative to the linear polarization when the laser beam was received previously. Polarizer 32 passes through the laser beam with the rotated linear polarization. Collimator 36 collimates and directs the laser beam to scanner 40. Scanner 40 manipulates the laser beam to control the xy-position of the focal point. Objective lens 42 directs the laser beam to target 24.

To aid in describing the embodiments, the xyz coordinate system of a laser system is described. The direction of the laser beam as the beam approaches the target defines the z-axis. The z-axis in turn defines an xy-plane. "Z-position" refers to a point of the z-axis; "xy-position" refers to a point of the xy-plane. Placement of the x- and y-axes on the xy-plane may be selected in any suitable manner. E.g., if target 24 is an eye of a patient, the x- or y-axis may be parallel to a vertical axis of the patient. The origin of the z-axis may be selected in any suitable manner. E.g., if target 24 is an eye, the origin may be the anterior surface of the eye, which may or may not be in contact with a patient interface.

To aid in describing the embodiments, optical devices are described. An optical device is a device that controls (e.g., reflects, refracts, filters, transmits (or passes through), and/or polarizes) light. The device can be made of any suitable material that controls the light as designed, e.g., glass, crystal, metal, or semiconductor. Examples of optical devices include lenses, mirrors, prisms, optical filters, waveguides, waveplates, expanders, collimators, splitters, gratings, and polarizers.

Example components of system 10 may be as follows. Laser 24 is a device that generates an intense beam of coherent monochromatic light by stimulated emission of photons from excited atoms or molecules. A laser beam may have any suitable wavelength, e.g., a wavelength in the infrared (IR) or ultraviolet (UV) range. The pulses of the laser beam may have a pulse duration in any suitable range, e.g., the nanosecond, picosecond, femtosecond, or attosecond range.

Beam expander 20 is one or more optical devices that expand the diameter of a laser beam and control the focal point of a laser beam. In the illustrated embodiment, beam expander 20 comprises mirror 22 and optical devices 30.

Mirror 22 is an optical device that reflects light, e.g., a laser beam. In the illustrated embodiment, mirror 22 has a surface curvature that can be adjusted to control the z-position of a focal point of a laser beam. Mirror 22 may be any suitable deformable mirror, e.g., a Revibro Optics deformable mirror. Mirror 22 is described in more detail with reference to FIGS. 2A and 2B.

Expander optical devices 30 are optical devices that direct the laser beam to mirror 22, and receive the laser beam reflected from mirror 22. In the illustrated embodiment, optical devices 30 include polarizer 32, waveplate 34, and collimator 36. Polarizer 32 is an optical filter that transmits light of a specific polarization while blocking light of other polarizations. It can convert light of undefined or mixed polarization into light with a single polarization state (linear, circular, or elliptic). In the illustrated embodiment, polarizer 32 reflects a laser beam with a first linear polarization towards waveplate 34, and transmits the laser beam with a second linear polarization. The relationship between the first and second polarizations can be selected such polarizer 32 can direct a beam towards mirror 22 (e.g., through waveplate 34) to be reflected by mirror 22, and then can pass through the reflected beam (e.g., through waveplate 34). In the illustrated embodiment, waveplate 34 changes the linear polarization of light beam by 90 degrees, so the difference between the first and second polarizations is 90 degrees.

Waveplate 34 is an optical device that alters the polarization state of a light travelling through it. Waveplate 34 may be any suitable waveplate, e.g., a quarter-wave plate, which converts linearly polarized light into circularly polarized light and vice versa, or a half-wave plate, which rotates linearly polarized light by 45 degrees. In the illustrated embodiment, waveplate 34 is a quarter-wave plate that receives the laser beam with a first linear polarization from polarizer 32, converts the laser beam from the first linear polarization to a circular polarization, and directs the laser beam to mirror 22. Waveplate 34 then receives the laser beam reflected from mirror 22, and converts the laser beam reflected from the mirror from the circular polarization to a second linear polarization rotated relative to first linear polarization. In the illustrated embodiment, waveplate 34 changes the original linear polarization of light beam by 90 degrees.

In another embodiment, waveplate 34 is a half-wave plate that receives the laser beam with a first linear polarization from polarizer 32, rotates the polarization of the laser beam by 45 degrees, and directs the laser beam to mirror 22. Waveplate 34 then receives the laser beam reflected from mirror 22, and rotates the polarization of the laser beam by 45 degrees to a second linear polarization rotated relative to first linear polarization. In the embodiment, waveplate 34 changes the original linear polarization of light beam by 90 degrees.

Collimator 36 is an optical device that produces a substantially or almost parallel beam of rays or radiation. After being reflected by mirror 22, the beam exhibits a strong divergence. Accordingly, collimator 36 collimates the laser beam and directs the laser beam to scanner 40.

Laser system 10 also includes scanner 40, objective lens 42, control electronics 44, and computer 46. Laser beam scanner 40 is one or more optical devices that control the direction of a laser beam to control the xy-position of the focal point. To transversely deflect the laser beam, scanner 40 may have a pair of galvanometric actuated scanner mirrors that tilt about mutually perpendicular axes. In the illustrated embodiment, scanner 40 receives the laser beam from the beam expander 20, and manipulates the laser beam to control the xy-position of the focal point. Objective lens 42 receives the laser beam from the scanner 40 and directs the beam to target 24.

Computer 46 receives a depth instruction and adjusts one or more actuation parameters of control electronics 44 to control the surface curvature of mirror 22 according to the depth instruction. A depth instruction describes desired z-positions of the laser beam, including depths of the focal point into target 24. The instruction may be based on user input or commands of a software program. For example, a user may input a specific depth of the focal point onto or into target 24, and the instruction may reflect that depth. As another example, a software program may direct computer 46 to vary the z position (and perhaps the xy position) of the focal point to create photodisruptions on or within target 24 according to a specified pattern. As another example, a software program may vary the focal point within a range to detect a particular effect (e.g., highest reflectance) in the range.

Control electronics 44 receives instructions from computer 46 and applies voltages to mirror 22 to change the curvature of mirror 22 according to the instructions. In certain embodiments, control electronics 44 includes an electrical amplifier that receives a low voltage (e.g., 0-10 V) signal and provides the high voltage signal (e.g., 0-400 V) to operate mirror 22. To control aberration, the amplifier can control several zones with a low voltage signal per zone.

Figure 2A:
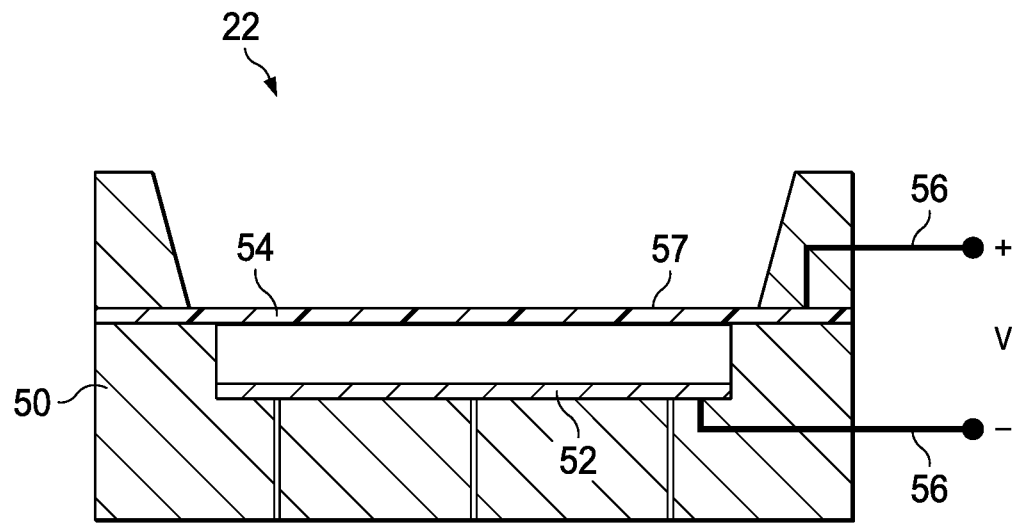
FIGS. 2A through 2C illustrate an embodiment of a mirror.
Figure 2B:
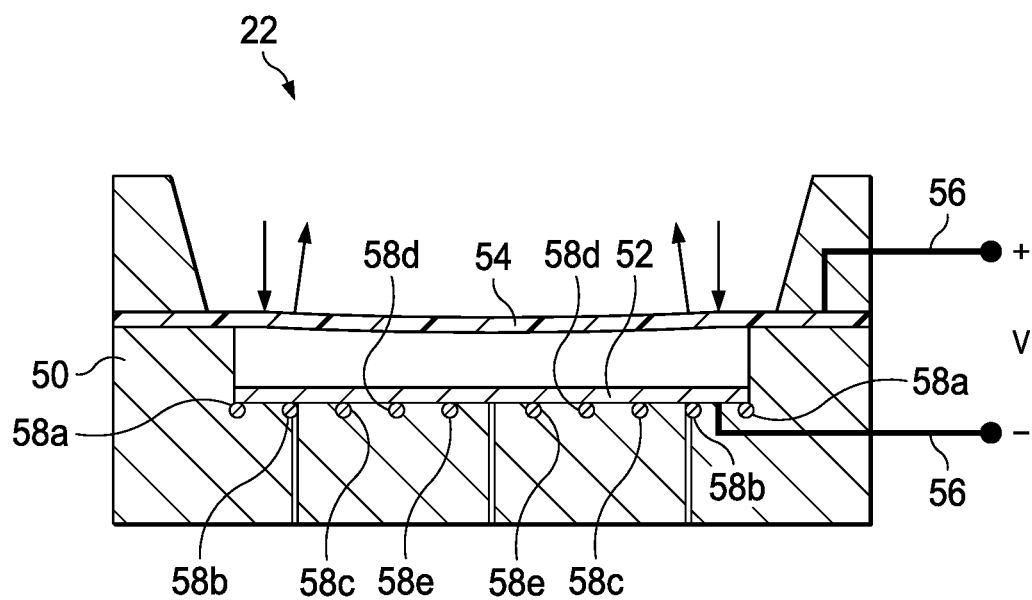
Figure 2C:
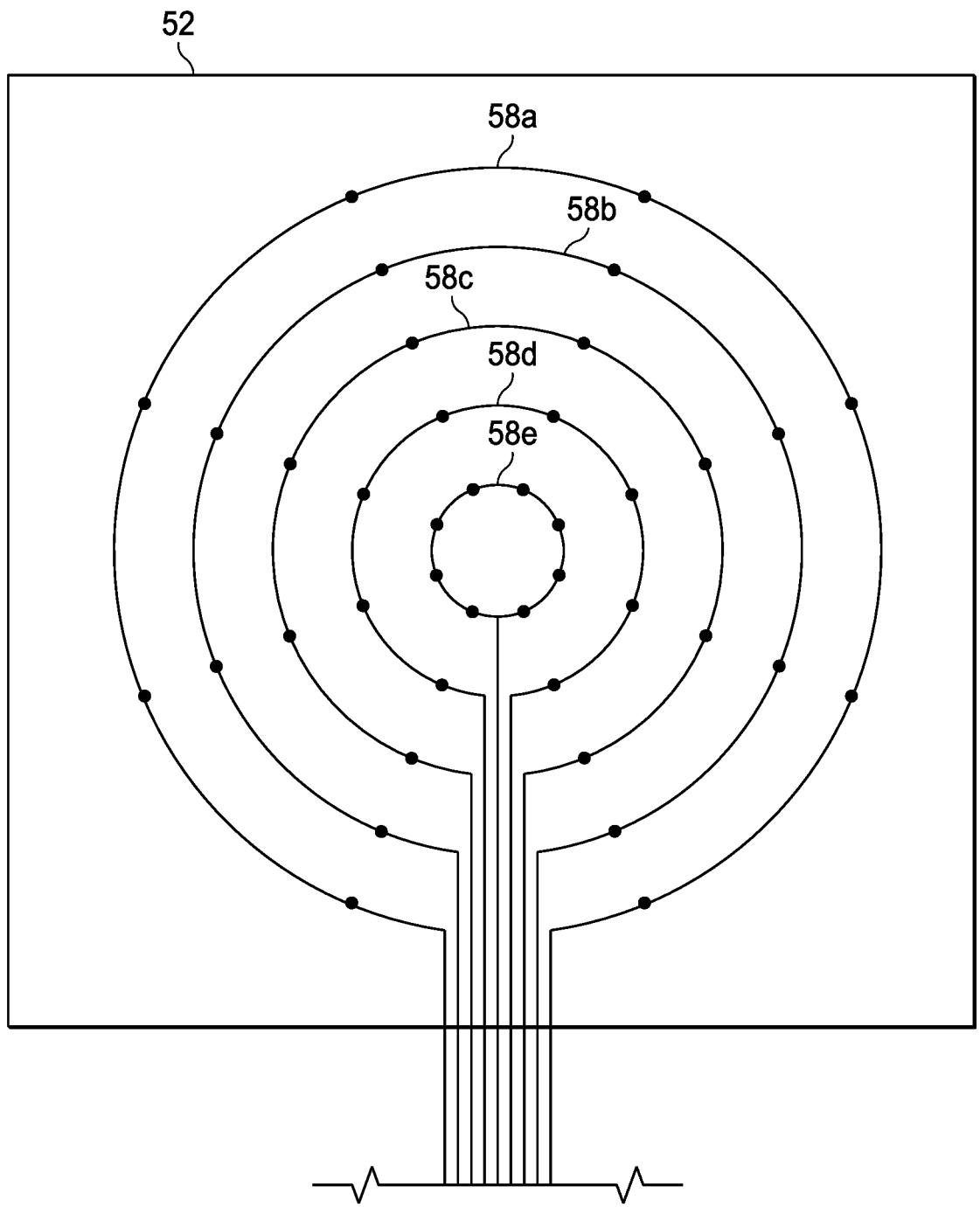

FIGS. 2A through 2C illustrate an embodiment of mirror 22. FIGS. 2A and 2B illustrate a cross-sectional view of mirror 22. Mirror 22 may have any suitable diameter e.g., 2 to 4 mm. The focal length of mirror 22 may be varied through any suitable range, e.g., 65 mm to infinity.

Mirror 22 includes a housing 50, an electrode plate 52, a membrane 54, and connectors 56, coupled as shown. Housing 50 provides structural support for the components of mirror 22 and may be made of any suitable stiff material. Membrane 54 may comprise a flexible material, such as a polymer. Membrane 54 has a reflective surface 57, which in system 10 is the surface that reflects the laser beam. Reflective surface 57 may have any suitable diameter, e.g., 3 to 5 mm, and may be metallic, e.g., aluminum, gold, or silver. Connectors 56 are used to apply a voltage between membrane 54 and electrode plate 52, and may be any suitable conductive material.

FIG. 2C illustrates an example of electrode plate 52. Electrode plate 52 includes electrodes 58 (58a-e) that, when activated, controls the curvature of reflective surface 57. Electrode plate 52 may have any suitable number of electrodes 58 of any suitable shape. In the example, five electrodes 58 form five concentric rings. However, electrode plate 52 may have more or fewer electrodes 58 of any suitable shape, e.g., circle, oval, or square.

FIG. 2B illustrates when a voltage is applied between membrane 54 and electrode plate 52, and the curvature of surface 57 changes in response to the electrostatic actuation. Computer 46 sends instructions that control actuation parameters of control electronics 44 to control the surface curvature of mirror 22. An actuation parameter may operate to apply a particular voltage to a specific electrode 58, e.g., a value of the parameter for electrode 58a may specify the particular voltage to apply to electrode 58a. Any suitable voltage may be applied. In this embodiment, the voltage may be in the range of 0 to 400 V.

In the illustrated example, computer 46 instructs control electronics 44 to apply a first voltage to electrode 58a that attracts membrane 54 towards plate 52 and a second voltage to electrode 58b that repels membrane 54 away from plate 52. In other examples, computer 46 instructs control electronics 44 to apply voltages to electrodes 58a-e that attract membrane 54 towards plate 52 to yield surface 57 with a concave shape. The deflection may be greater at the center, so the voltage for electrode 58e may be greater than that for electrodes 58a-d, the voltage for electrode 58d may be greater than that for electrodes 58a-c, and so on.

The actuation parameters for a surface curvature that yields a specific z-position of the focal point may be determined in any suitable manner. For example, the curvature may be changed as the laser beam is applied to a test material to determine a curvature that corresponds to a z-position within the material. The curvature may be decreased to move the focal point closer to objective lens 42 curvature and/or increased to move the focal point away from objective lens 42. The actuation parameter values that yield corresponding z-positions are recorded for use by computer 46.

Figure 3:
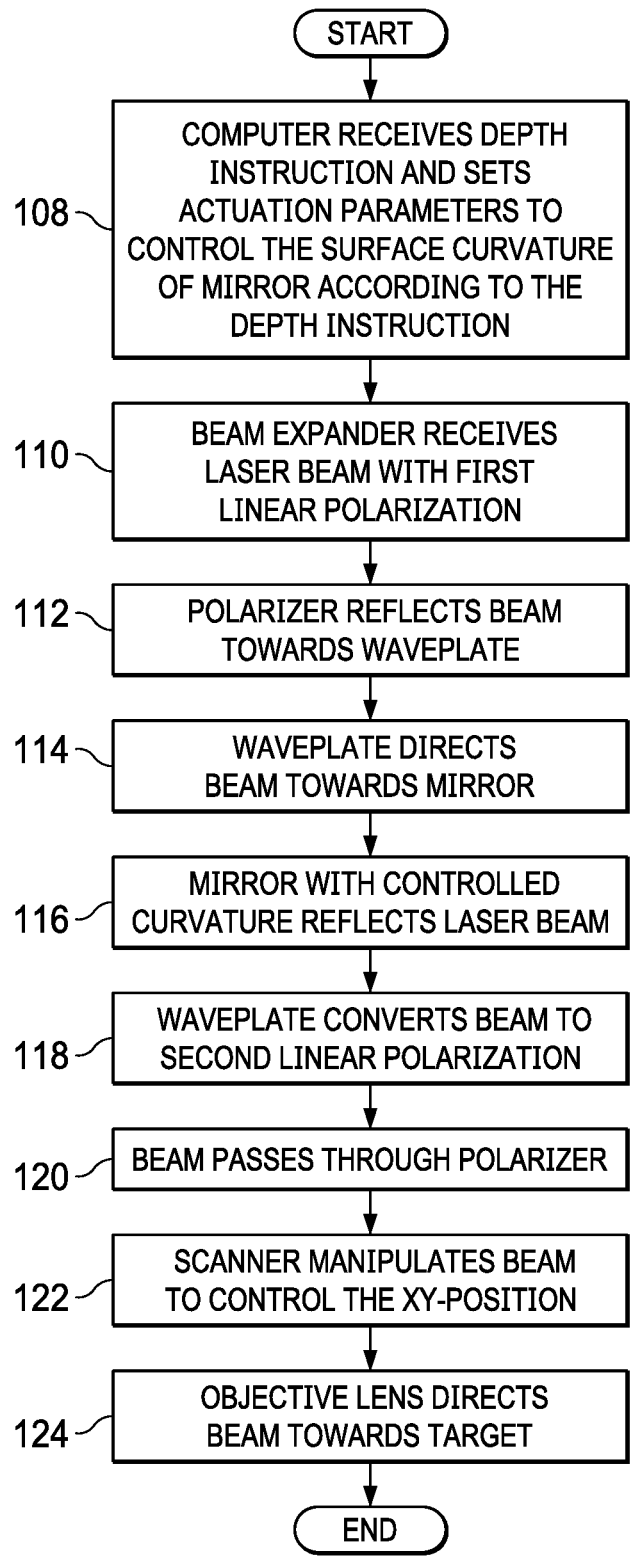
FIG. 3 illustrates a method for controlling a position of a focal point of a laser beam directed to a target that may be performed by the system of FIG. 1.

FIG. 3 illustrates a method for controlling a position of a focal point of a laser beam directed to target 24 that may be performed by system 10 of FIG. 1. The method starts at step 108, where computer 46 receives a depth instruction and sets actuation parameters to control the surface curvature of the mirror according to the depth instruction. Beam expander 20 receives a laser beam with a first linear polarization from laser 26 at step 110. Beam expander 20 comprises mirror 22 and expander optical devices 30, which comprise polarizer 32 and waveplate 34. Polarizer 32 reflects the laser beam with the first linear polarization towards waveplate 34 at step 112.

Waveplate 34 directs the laser beam towards mirror 22 at step 114. If waveplate 34 is a quarter-wave plate, waveplate 34 converts the laser beam from the first linear polarization to a circular polarization. If waveplate 34 is a half-wave plate, waveplate 34 rotates the first linear polarization by 45 degrees.

Mirror 22 has a surface curvature that is controlled to reflect the laser beam at step 116 to yield the focal point of the laser beam at a predetermined z-position. Mirror 22 operates as described with reference to FIGS. 2A-C. Mirror 22 reflects the beam towards waveplate 34.

Waveplate 34 converts the laser beam to a second linear polarization rotated relative to the first linear polarization at step 118. If waveplate 34 is a quarter-wave plate, waveplate 34 converts the laser beam reflected from mirror 22 from the circular polarization to the second linear polarization. If waveplate 34 is a half-wave plate, waveplate 34 rotates the polarization of the laser beam reflected from mirror 22 by 45 degrees to the second linear polarization.

The laser beam with the second linear polarization passes through polarizer 32 at step 120. Scanner 40 manipulates the laser beam to control the xy-position of the focal point at step 122. Objective lens 42 directs the beam towards target 24 at step 124. The method ends.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors (e.g., a chip that resides in computers). Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed:

1. A system for controlling a position of a focal point of a laser beam directed to a target, comprising:
   a beam expander configured to control the focal point of the laser beam, and comprising:
     a mirror with a surface curvature that can be adjusted to control a z-position of the focal point along a z-axis of an xyz coordinate system, the z-axis defined by the laser beam; and
     one or more expander optical devices configured to:
       direct the laser beam towards the mirror; and
       receive the laser beam reflected from the mirror;
   a scanner configured to:
     receive the laser beam from the beam expander; and
     manipulate the laser beam to control an xy-position of the focal point in an xy-plane defined by the z-axis;
   an objective lens configured to:
     receive the laser beam from the scanner; and
     direct the laser beam towards the target; and
   a computer configured to:
     receive a depth instruction; and
     set one or more actuation parameters to control the surface curvature of the mirror according to the depth instruction;
   wherein the expander optical devices comprise a polarizer configured to:
     receive the laser beam with a first linear polarization;
     direct the laser beam with the first linear polarization towards a waveplate;
     receive the laser beam with a second linear polarization; and
     pass through the laser beam with the second linear polarization.

2. The system of claim 1, wherein the waveplate is configured to:
   receive the laser beam from the polarizer with the first linear polarization;
   direct the laser beam towards the mirror;
   receive the laser beam reflected from the mirror; and
   convert the laser beam reflected from the mirror to the second linear polarization rotated relative to the first linear polarization.

3. The system of claim 1, wherein the difference between the first and second polarizations is 90 degrees.

4. The system of claim 2, wherein the waveplate comprises a quarter-wave plate configured to:
   receive the laser beam from the polarizer with the first linear polarization;
   convert the laser beam from the first linear polarization to a circular polarization;
   direct the laser beam towards the mirror;
   receive the laser beam reflected from the mirror; and
   convert the laser beam reflected from the mirror from the circular polarization to the second linear polarization.

5. The system of claim 2, wherein the waveplate comprises a half-wave plate configured to:
   receive the laser beam from the polarizer with the first linear polarization;
   rotate the first linear polarization by 45 degrees;
   direct the laser beam towards the mirror;
   receive the laser beam reflected from the mirror; and
   rotate the polarization of the laser beam reflected from the mirror by 45 degrees to the second linear polarization.

6. The system of claim 1, wherein the expander optical devices comprise a collimator configured to:
   collimate the laser beam; and
   direct the laser beam towards the scanner.

7. The system of claim 1, wherein depth instruction specifies the z-position for the focal point.

8. The system of claim 1, wherein depth instruction is an instruction to increase or decrease from the current z-position of the focal point.

9. A method for controlling a position of a focal point of a laser beam directed to a target, comprising:
   receiving, at a computer, a depth instruction;
   setting one or more actuation parameters to control a surface curvature of a mirror according to the depth instruction;
   receiving the laser beam at a beam expander comprising the mirror and one or more expander optical devices, the mirror having a surface curvature that can be adjusted to control a z-position of the focal point along a z-axis of an xyz coordinate system, the z-axis defined by the laser beam;
   directing, by the one or more expander optical devices, the laser beam towards the mirror;
   reflecting, by the mirror, the laser beam with the surface curvature to control the z-position of the focal point;
   receiving, at the one or more expander optical devices, the laser beam reflected from the mirror;
   receiving, at a scanner, the laser beam from the beam expander;
   manipulating the laser beam to control an xy-position of the focal point in an xy-plane defined by the z-axis;
   receiving, at an objective lens, the laser beam from the scanner; and
   directing the beam towards the target;
   wherein the one or more expander optical devices comprises a polarizer;
   directing, by the one or more expander optical devices, the laser beam towards the mirror further comprises:
     receiving, at the polarizer, the laser beam with a first linear polarization; and
     directing the laser beam with the first linear polarization to a waveplate; and receiving, at the one or more expander optical devices, the laser beam reflected from the mirror further comprises:
  receiving the laser beam with a second linear polarization; and
passing through the laser beam with the second linear polarization.

10. The method of claim 9, further comprising:
receiving, at the waveplate, the laser beam from the polarizer with the first linear polarization;
directing the laser beam towards the mirror;
receiving, at the waveplate, the laser beam reflected from the mirror; and
converting the laser beam reflected from the mirror to the second linear polarization rotated relative to the first linear polarization.

11. The method of claim 10, wherein:
the waveplate comprises a quarter-wave plate;
receiving, at the waveplate, the laser beam from the polarizer with the first linear polarization further comprises:
  converting the laser beam from the first linear polarization to a circular polarization; and
converting, by the waveplate, the laser beam reflected from the mirror to the second linear polarization rotated relative to the first linear polarization further comprises:
  converting the laser beam reflected from the mirror from the circular polarization to the second linear polarization.

12. The method of claim 10, wherein:
the waveplate comprises a half-wave plate;
receiving, at the waveplate, the laser beam from the polarizer with the first linear polarization further comprises:
  rotating the first linear polarization by 45 degrees; and
converting, by the waveplate, the laser beam reflected from the mirror to the second linear polarization rotated relative to the first linear polarization further comprises:
  rotating the polarization of the laser beam reflected from the mirror by 45 degrees to the second linear polarization.

* * * * *